United States Patent
Kim et al.

(10) Patent No.: US 10,633,698 B2
(45) Date of Patent: Apr. 28, 2020

(54) COMPOSITION FOR PCR CONTAINING A POLYETHYLENE GLYCOL-ENGRAFTED NANO-SIZED GRAPHENE OXIDE

(71) Applicant: KONKUK UNIVERSITY INDUSTRIAL COOPERATION CORP, Seoul (KR)

(72) Inventors: Dong Eun Kim, Seoul (KR); Hyo Ryoung Kim, Seoul (KR); Ah Ruem Baek, Daejeon (KR)

(73) Assignee: KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 224 days.

(21) Appl. No.: 15/829,432

(22) Filed: Dec. 1, 2017

(65) Prior Publication Data

US 2018/0155765 A1    Jun. 7, 2018

(30) Foreign Application Priority Data

Dec. 2, 2016 (KR) .................. 10-2016-0163558

(51) Int. Cl.
| | | |
|---|---|---|
| *C12P 19/34* | (2006.01) | |
| *C12Q 1/686* | (2018.01) | |
| *C01B 32/198* | (2017.01) | |
| *C08L 71/08* | (2006.01) | |
| *C08L 71/02* | (2006.01) | |
| *C12Q 1/6853* | (2018.01) | |

(52) U.S. Cl.
CPC ............ *C12Q 1/686* (2013.01); *C01B 32/198* (2017.08); *C08L 71/02* (2013.01); *C08L 71/08* (2013.01); *C12Q 1/6853* (2013.01)

(58) Field of Classification Search
CPC  C12Q 1/686; C12Q 2527/125; C12Q 1/6853; C12Q 1/6818; C12Q 1/6888; C12Q 1/70; C12Q 2527/137
USPC ...................................................... 435/91.2
See application file for complete search history.

(56) References Cited

U.S. PATENT DOCUMENTS

2002/0037504 A1    3/2002    Arahira et al.

FOREIGN PATENT DOCUMENTS

| KR | 10-2006-0070697 | 6/2006 |
| KR | 10-2007-0112654 | 11/2007 |
| KR | 10-2012-0097793 | 9/2012 |
| KR | 10-1540175 | 7/2015 |

OTHER PUBLICATIONS

Feng et al., SMALL, 9(11), 1989-1997, (Year: 2013).*
Weiner et al., Biotechniques 44;701-704, April (Year: 2008).*
Sun et al., Nano Res, 1(3): 203-212 (Year: 2008).*
Hong et al., "Fluorometric Detection of MicroRNA Using Isothermal Gene Amplification and Graphene Oxide." *Analytical Chemistry* 2016; 88(6): 2999-3003.
Kim et al., "Facilitation of Polymerase Chain Reaction with Poly-(ethylene glycol)-Engrafted Graphene Oxide Analogous to a Single-Stranded-DNA Binding Protein," *ACS Applied Materials & Interfaces*, 2016; 8:33521-33528.
Liu et al., "PEGylated Nanographene Oxide for Delivery Of Water-Insoluble Cancer Drugs." *Journal of the American Chemical Society* 2008; 130(33): 10876-10877.
Lou, Xinhui, and Ying Zhang. "Mechanism Studies on Nanopcr and Applications Of Gold Nanoparticles in Genetic Analysis." *ACS Applied Materials & Interfaces* 2013; 5(13): 6276-6284.
Roh et al., "A Simple PCR-Based Fluorometric System for Detection of Mutant Fusion DNAs Using a Quencher-Free Fluorescent DNA Probe and Graphene Oxide." *Chemical Communications* 2015; 51(32): 6960-6963.
Tan et al., "Functionalization Of Graphene Oxide Generates A Unique Interface For Selective Serum Protein Interactions." *ACS Applied Materials & Interfaces* 2013; 5(4): 1370-1377.

* cited by examiner

*Primary Examiner* — Cynthia B Wilder
(74) *Attorney, Agent, or Firm* — Norton Rose Fulbright US LLP

(57) ABSTRACT

Disclosed are a composition for PCR including polyethylene glycol-engrafted nano-sized graphene oxide (PEG-nGO), the composition for PCR being capable of increasing the efficiency and specificity of PCR and shortening PCR time, and a PCR method using the same.

8 Claims, 14 Drawing Sheets

Specification includes a Sequence Listing.

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: GAPDH forward primer

<400> SEQUENCE: 1
ttgttgccat caatgacccc ttcattgacc                                    30

<210> SEQ ID NO 2
<211> LENGTH: 25
<212> TYPE: DNA
<213> ORGANISM: Artificial Sequence
<220> FEATURE:
<223> OTHER INFORMATION: GAPDH reverse primer

<400> SEQUENCE: 2
cttcccgttc tcagccttga cggtg                                         25

<210> SEQ ID NO 3
<211> LENGTH: 20
<212> TYPE: DNA
<213> ORGANISM: Artificial Sequence
<220> FEATURE:
<223> OTHER INFORMATION: pET22b linear forward primer

<400> SEQUENCE: 3
gtgtctctta tcagaccgtt                                               20

<210> SEQ ID NO 4
<211> LENGTH: 19
<212> TYPE: DNA
<213> ORGANISM: Artificial Sequence
<220> FEATURE:
<223> OTHER INFORMATION: pET22b linear reverse primer 102bp

<400> SEQUENCE: 4
tgtaattcag ctccgccat                                                19

<210> SEQ ID NO 5
<211> LENGTH: 17
<212> TYPE: DNA
<213> ORGANISM: Artificial Sequence
<220> FEATURE:
<223> OTHER INFORMATION: pET22b linear reverse primer 198bp

<400> SEQUENCE: 5
caatttgcga cggcgcg                                                  17

<210> SEQ ID NO 6
<211> LENGTH: 21
<212> TYPE: DNA
```

```
<213> ORGANISM: Artificial Sequence
<220> FEATURE:
<223> OTHER INFORMATION: pET22b linear reverse primer 401bp

<400> SEQUENCE: 6
aaataacgcc ggaacattag t                                              21

<210> SEQ ID NO 7
<211> LENGTH: 20
<212> TYPE: DNA
<213> ORGANISM: Artificial Sequence
<220> FEATURE:
<223> OTHER INFORMATION: pET22b linear reverse primer 805bp

<400> SEQUENCE: 7
taacatgagc tgtcttcggt                                                20

<210> SEQ ID NO 8
<211> LENGTH: 18
<212> TYPE: DNA
<213> ORGANISM: Artificial Sequence
<220> FEATURE:
<223> OTHER INFORMATION: pET22b linear reverse primer 1600bp

<400> SEQUENCE: 8
acataatggt gcagggcg                                                  18
```

COMPOSITION FOR PCR CONTAINING A POLYETHYLENE GLYCOL-ENGRAFTED NANO-SIZED GRAPHENE OXIDE

CROSS-REFERENCE TO RELATED APPLICATION

This application claims priority to and the benefit of Korean Patent Application No. 10-2016-0163558, filed on Dec. 2, 2016, the disclosure of which is incorporated herein by reference in its entirety.

BACKGROUND

1. Field of the Invention

The present invention relates to a composition for PCR including polyethylene glycol-engrafted nano-sized graphene oxide (PEG-nGO), the composition for PCR being capable of increasing the efficiency and specificity of PCR and shortening PCR time, and a PCR method using the same.

2. Discussion of Related Art

Polymerase chain reaction (PCR) is a method of artificially amplifying DNA and is an indispensable technology in modern biotechnology and molecular biology. PCR is widely used in diagnostics, gene manipulation, biosensors, and a variety of fields. However, the specificity and efficiency of PCR may be reduced due to unintended (re) annealing of single stranded DNA (e.g., primer dimerization, incorrect primer binding, and reannealing of PCR amplicons). Nonspecific primer binding in PCR steps may result in generation of a large number of nonspecific amplicons, which can be confirmed by agarose gel electrophoresis. That is, smearing of a PCR band, which is observed in an electrophoresed agarose gel, indicates the presence of a large number of DNAs having similar sizes (i.e., nonspecific amplicons). When a DNA template is excessively amplified in PCR and the same primers are used in the second or subsequent PCR, nonspecific amplicons may be generated. To solve these problems, various PCR techniques such as nested PCR have been developed. In the first step of nested PCR, a primer set for amplifying a broad range including a target sequence on a DNA template is used, and in the second step, primer sequences for amplifying only the target sequence are generally used as an inner primer (nested primer) set.

In addition, studies have been conducted to increase the efficiency and specificity of PCR using various nanomaterials such as gold nanoparticles, carbon nanotubes, carbon nanopowder, graphene nanoflakes, cadmium telluride quantum dots, graphene quantum dots, dendrimers, and titanium dioxide. For example, graphene nanoflakes serve to improve PCR efficiency by increasing thermal conductivity of a PCR mixture, and gold nanoparticles are capable of being adsorbed to DNA and proteins to reduce amplification of nonspecific DNA products. However, these methods have a disadvantage that the specificity and efficiency of PCR may not be fundamentally solved when each nanoparticle is present. It is also controversial as to whether gold nanoparticles play a role in increasing the specificity of PCR.

Graphene oxide (GO) refers to a material having a honeycomb-like nanostructure in which carbons are arranged in a hexagonal lattice, and is prepared by oxidizing a single layer of graphite, i.e., graphene. The surface of GO may have various functional groups such as epoxy groups, hydroxyl groups, and carboxyl groups, which allow the GO to be dissolved in a water-soluble solvent. In addition, GO may bind to single-stranded nucleic acids via π stacking interaction and hydrogen bonding, but has low affinity to double-stranded nucleic acids. Based on the functions of GO, GO has been widely applied in various areas such as DNA detection, biosensors based on energy transfer through fluorescence resonance, and real-time monitoring of fluorescently labeled nucleic acids.

However, GO is not soluble in a buffer solution containing $Mg^{2+}$ and a high salt concentration, such as a PCR buffer, and is adsorbed to proteins such as a DNA polymerase via non-covalent bonding. It is well known that divalent cations such as $Mg^{2+}$ induce strong crosslinking between GO sheets, allowing the GO sheets to be aggregated. That is, when other salts are added to a PCR sample for buffering, GO sheets may be aggregated by divalent cations such as $Mg^{2+}$. In addition, it has been reported that GO is bound to proteins to induce protein aggregation, which may distort the structures of proteins and cause the loss of function of proteins. Polyethylene glycol (PEG) is known as a biocompatible polymer that reduces protein adsorption. Recently, to minimize nonspecific protein adsorption and increase the solubility of GO in a solution with a high salt concentration, nano-sized GO (nGO) was prepared, and the surface of the nGO was coated with PEG to prepare PEG-nGO (Non-Patent Document 1). In Non-Patent Document 1, it is disclosed that, when PEG-nGO interacts with a protein, a nano-bio interface may be formed due to PEGylation of the surface of GO, thereby significantly reducing adsorption of the PEG-nGO to the protein. Accordingly, PEG-nGO is attracting attention as a substance capable of interacting with proteins without impairing the structure and function of the proteins.

Therefore, the present inventors have tried to confirm the effect of PEG-nGO on the efficiency and specificity of PCR. During the denaturation step of PCR, polyethylene glycol-engrafted nano-sized graphene oxide (PEG-nGO) was capable of being adsorbed to single-stranded primers and a DNA template. Accordingly, when PEG-nGO was added to a PCR sample and PCR amplification was performed, in an initial PCR process in which an excessive amount of primers was included, primer dimerization was inhibited, and in a late PCR process in which amplified PCR products were accumulated, nonspecific reannealing between the amplified PCR products and other DNA strands was inhibited. Thus, it was confirmed that, when PCR was performed using a composition for PCR including the PEG-nGO of the present invention, the efficiency and specificity of PCR may be improved and PCR time may be shortened as compared with conventional PCR techniques. By confirming these results, the present invention was completed.

SUMMARY OF THE INVENTION

Therefore, to solve the above problems, when a PCR sample was prepared by adding PEG-nGO and PCR amplification was performed on the prepared PCR sample, in an initial PCR process in which an excessive amount of primers was included, primer dimerization was inhibited, and in a late PCR process in which amplified PCR products were accumulated, nonspecific reannealing between the amplified PCR products and other DNA strands was inhibited. By confirming these results, the present invention was completed.

Therefore, it is an objective of the present invention to provide a composition for PCR capable of improving the speed and accuracy of PCR by increasing the efficiency and specificity of PCR, a PCR kit including the same, and a PCR method using the same.

In accordance with the present invention, the above and other objectives can be accomplished by the provision of a composition for PCR including polyethylene glycol-engrafted nano-sized graphene oxide (PEG-nGO), and a PCR kit including the same.

In a preferred embodiment of the present invention, the PEG-nGO may be present at a concentration of 1 to 10 µg/ml.

In a preferred embodiment of the present invention, each forward and reverse primer may be added to the composition for PCR at a concentration of 0.1 to 1.0 µM.

In a preferred embodiment of the present invention, the PEG-nGO may increase the efficiency and specificity of PCR by inhibiting primer dimerization and nonspecific binding of amplified amplicons, and may promote denaturation of double-stranded DNA in a sample to shorten PCR time.

In accordance with an aspect of the present invention, the above and other objectives can be accomplished by the provision of a PCR method including the following steps i) and ii):

i) a step of preparing a PCR sample by mixing a DNA template, dNTPs, a DNA polymerase, and forward and reverse primers for amplifying a target sequence with the composition for PCR of the present invention; and ii) a step of performing PCR using the prepared PCR sample.

In a preferred embodiment of the present invention, PCR in step ii) may be selected from the group consisting of quantitative PCR (qPCR), real-time PCR, reverse transcription PCR (RT-PCR), solid phase PCR, competitive PCR, overlap-extension PCR, multiplex PCR, nested PCR, inverse PCR, ligation-mediated PCR, intersequence-specific PCR (ISSR), methylation-specific PCR (MSP), colony PCR, miniprimer PCR, nanoparticle-assisted PCR (nanoPCR), thermal asymmetric interlaced PCR (TAIL-PCR), touchdown PCR (step-down PCR), hot start PCR, in-silico PCR, allele-specific PCR, assembly PCR, asymmetric PCR, dial-out PCR, digital PCR (dPCR), and helicase-dependent amplification.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1A is a diagram showing the role of single-stranded binding proteins (SSBs) in protecting single-stranded DNA during intracellular DNA replication;

FIG. 1B is a diagram showing the structure of the PEG-nGO; and

FIG. 1C is a schematic diagram of PCR depending on whether the PEG-nGO of the present invention is added or not;

FIG. 2A includes images and graphs showing the results of AFN analysis for confirming particle sizes of GO, nGO, and PEG-nGO; and FIG. 2B is a graph showing the result of FT-IR analysis for confirming a characteristic of the particles of GO, nGO, and PEG-nGO;

FIG. 3A is an image showing the degree of PCR amplification depending on the concentration of GO, nGO, or PEG-nGO when PCR was performed on a sample containing GO, nGO, or PEG-nGO;

FIG. 3B is an image showing the degree of PCR amplification when PCR was performed on a sample containing PEG-nGO (PEG and nGO were combined) or a sample containing PEG+nGO (PEG and nGO were mixed);

FIG. 3C is a graph showing the result for confirming binding affinity between GO, nGO, or PEG-nGO and ssDNA; and FIG. 3D is an image showing the result for confirming binding affinity between GO, nGO, or PEG-nGO and Taq DNA polymerase;

FIG. 4A is an image showing the result for confirming the optimal concentration of PEG-nGO when adding the PEG-nGO to a PCR sample;

FIG. 4B is an image showing the result for confirming formation of amplicons depending on the presence or absence of PEG-nGO. PCR products obtained in the first round of PCR are diluted stepwise, and the second round of PCR was performed on the diluted PCR products with or without PEG-nGO;

FIG. 4C is an image showing the result for confirming formation of amplicons depending on the presence or absence of PEG-nGO when five rounds of PCR were consecutively performed; and FIG. 4D is an image showing the result for confirming formation of amplicons when PEG-nGO was additionally added to a PCR sample obtained from four rounds of consecutively-performed PCR, and the fifth round of PCR was performed;

FIG. 5A is an image showing the result of DNA amplification depending on the presence or absence of PEG-nGO in PCR samples to which various concentrations of primers were added; and FIG. 5B is an image showing the result for confirming the generation of primer dimers depending on the concentrations of PEG-nGO and primers in PCR samples not containing DNA templates;

FIG. 7A is an image showing the result of PCR performed by adding PEG-nGO in the second round without adding the PEG-nGO in the first round, Here, -Taq represents a control sample that does not contain Taq DNA polymerase;

FIG. 7B includes graphs showing the results for confirming the degree of denaturation of double-stranded DNA depending on the concentration of PEG-nGO added at various temperatures; and FIG. 7C includes images showing the results for confirming the pattern of DNA amplification depending on the presence or absence of PEG-nGO in a PCR process in which PCR rounds were shortened;

FIG. 8A is a schematic view showing annealing positions of a forward primer and a reverse primer designed to vary the amplification length of target DNA;

FIG. 8B is an image showing the result of performing PCR using a DNA plasmid as a DNA template without PEG-nGO;

FIG. 8C is an image showing the result of performing PCR on a PCR sample in which linear pET22b plasmid DNA was used as a template and PEG-nGO was not included; and FIG. 8D is an image showing the result of performing PCR on a PCR sample in which linear pET22b plasmid DNA was used as a template and PEG-nGO was included.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the present invention.

As described above, PCR is a method of artificially amplifying DNA and is widely used in modern biotechnology and molecular biology. However, the efficiency and specificity of PCR may be reduced when PCR is not performed under optimal conditions. Therefore, studies are underway to increase the efficiency and specificity of PCR.

Polyethylene glycol-engrafted nano-sized graphene oxide (PEG-nGO) included in the composition for PCR of the present invention functions as intracellular single-stranded binding proteins (SSBs) to bind to single-stranded DNA resulting from the denaturation of double-stranded DNA and to protect the same, and thus the PEG-nGO may improve the efficiency and specificity of PCR.

Therefore, the present invention provides a composition for PCR including polyethylene glycol-engrafted nano-sized graphene oxide (PEG-nGO).

In addition, the present invention provides a PCR kit including the composition for PCR.

As used herein, the term "PEG-nGO" refers to modified graphene oxide in which PEG is conjugated to graphene oxide prepared in the form of a nano-sized particle. The PEG-nGO may be prepared by a method that can be understood by a person skilled in the art to have a structure shown in FIG. 1B. Graphene oxide (GO) and the PEG-nGO of the present invention may be adsorbed to single-stranded DNA (ssDNA) and primers to prevent nonspecific binding and reannealing.

Figure 1A:
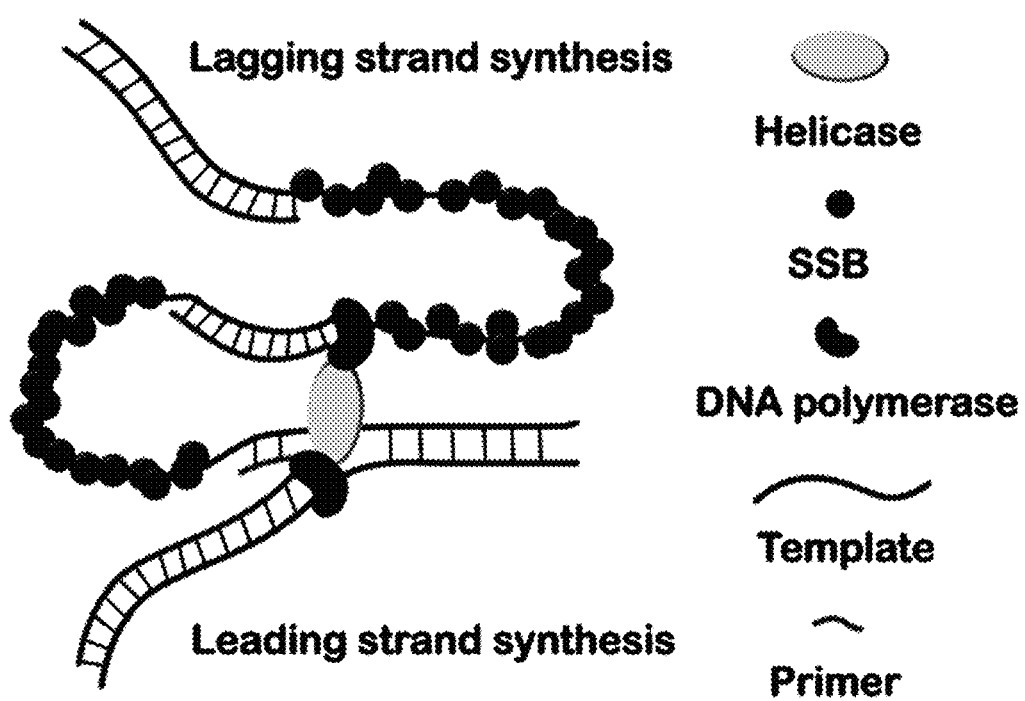
FIGS. 1A-1C includes schematic diagrams showing a process by which the efficiency and specificity of PCR may be increased by the polyethylene glycol-engrafted nano-sized graphene oxide (PEG-nGO) of the present invention.
Figure 1B:
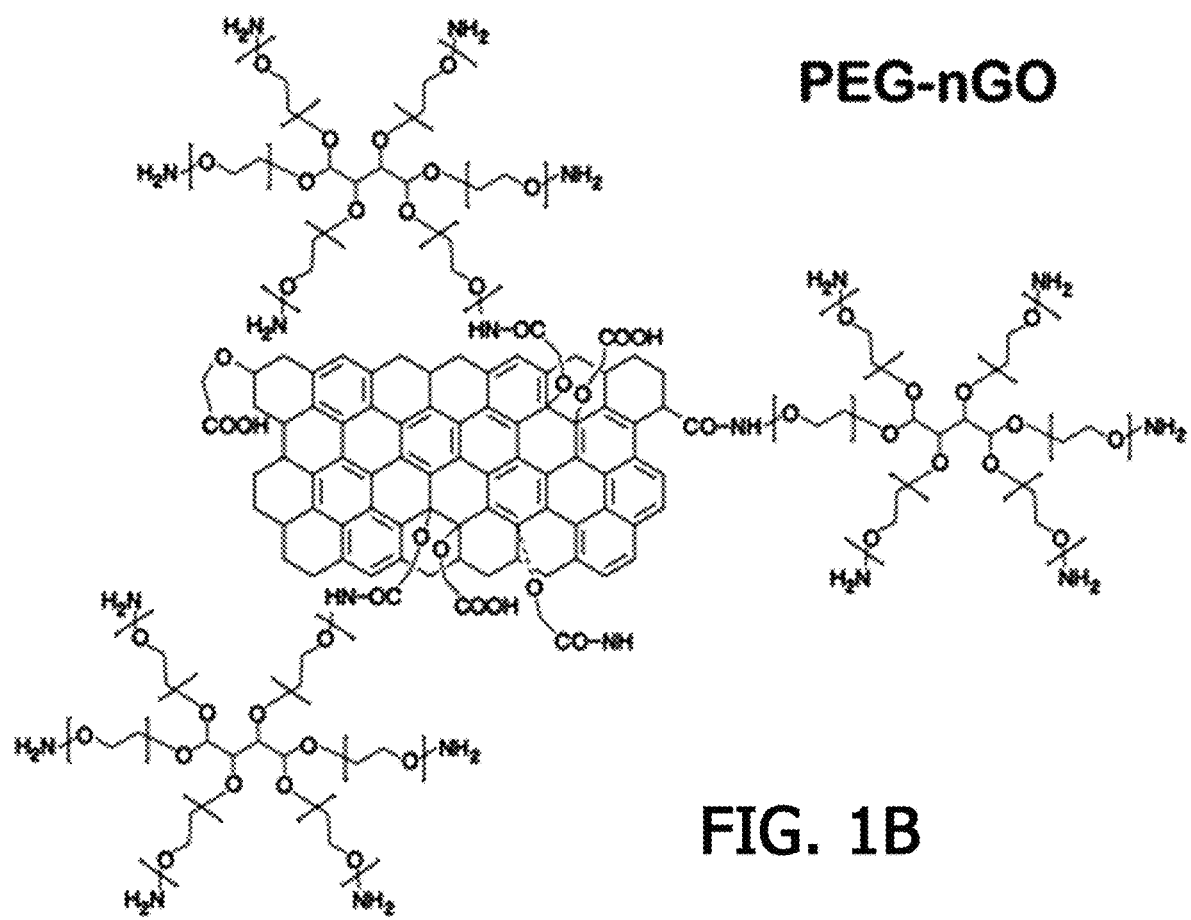
Figure 1C:
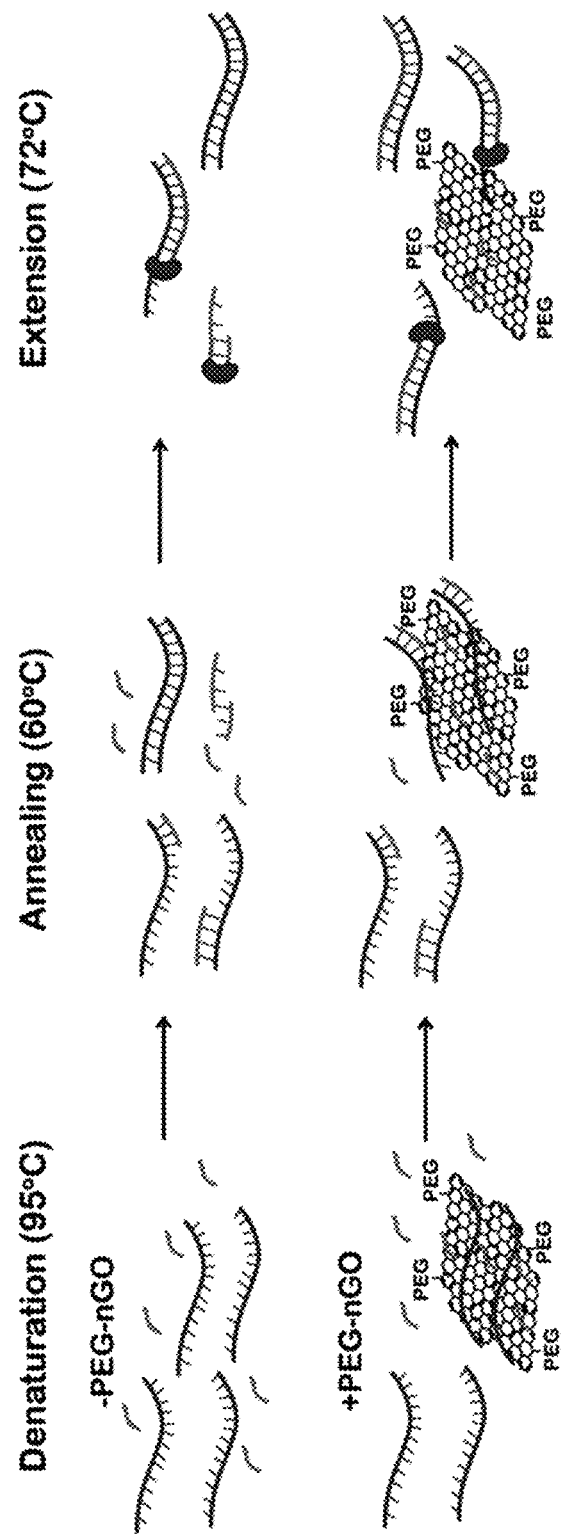

It is to be understood by those skilled in the art that the PEG-nGO serves as single-stranded binding proteins (SSBs) in a PCR sample. When DNA is amplified in the cell, SSBs bind to ssDNA separated from the template DNA and prevent ssDNA from being reannealed (FIG. 1A). In general, PCR is mainly used to amplify DNA in vitro. However, conventional compositions for PCR lack SSBs or other substances that can bind to ssDNA, including primers or amplified amplicons. Thus, during PCR, reannealing of amplified ssDNA may easily occur, which may lower the efficiency and specificity of PCR. Thus, the PEG-nGO of the present invention may act as an analog of SSB to improve the efficiency and specificity of PCR.

The PEG-nGO of the present invention is preferably contained in a sample at a concentration of 1 to 10 μg/ml. When the PEG-nGO is contained in a sample at a concentration of less than 1 μg/ml, nonspecific DNA may be amplified because the PEG-nGO may not be effectively adsorbed to primers or ssDNA. When the PEG-nGO is contained in a sample at a concentration exceeding 10 μg/ml, since the PEG-nGO is strongly adsorbed to DNA, there is a lack of primers and DNA templates used for DNA amplification, so that DNA amplification products may not be significantly obtained. In view of the present invention in which the PEG-nGO is used to increase the efficiency and specificity of PCR compared to conventional PCR techniques, the PEG-nGO is most preferably present at a concentration of 5 μg/ml in a sample, without being limited thereto. The concentration of the PEG-nGO may be experimentally determined by a typical technician. That is, when PCR products are subjected to agarose gel electrophoresis and a single DNA band is observed, it may be judged that the concentration of the PEG-nGO used in PCR is appropriate.

As used herein, a "composition for PCR" may additionally include PCR elements required for general PCR, such as a DNA polymerase, dNTPs, a DNA template, and primers. The primer may be synthesized by a conventional method to obtain an amplification product by complementarily binding to target DNA to be amplified. The primer refers to a single-stranded oligonucleotide complementary to a nucleic acid sequence to be replicated and may serve as a starting point for synthesis of a primer-mediated extension product. The length and sequence of the primer should be determined to be suitable for synthesis of an extended product. The specific length and sequence of the primer depend on primer usage conditions such as temperature and ionic strength, as well as the complexity of target DNA or RNA.

When performing PCR using the composition for PCR of the present invention, both forward and reverse primers are preferably contained in a PCR sample. In this case, each forward and reverse primer is preferably present at a concentration of 0.1 to 1.0 μM, without being limited thereto. The concentration of the primers may be experimentally determined by a typical technician. That is, when PCR products are subjected to agarose gel electrophoresis and a single DNA band is observed, it may be judged that the concentration of the primers used in PCR is appropriate.

In a specific embodiment of the present invention, the present inventors first prepared PEG-nGO to confirm whether PCR efficiency was increased when the PEG-nGO was added. The prepared PEG-nGO was found to be thicker than GO and nGO due to PEG bonding (FIG. 2).

Figure 3A:
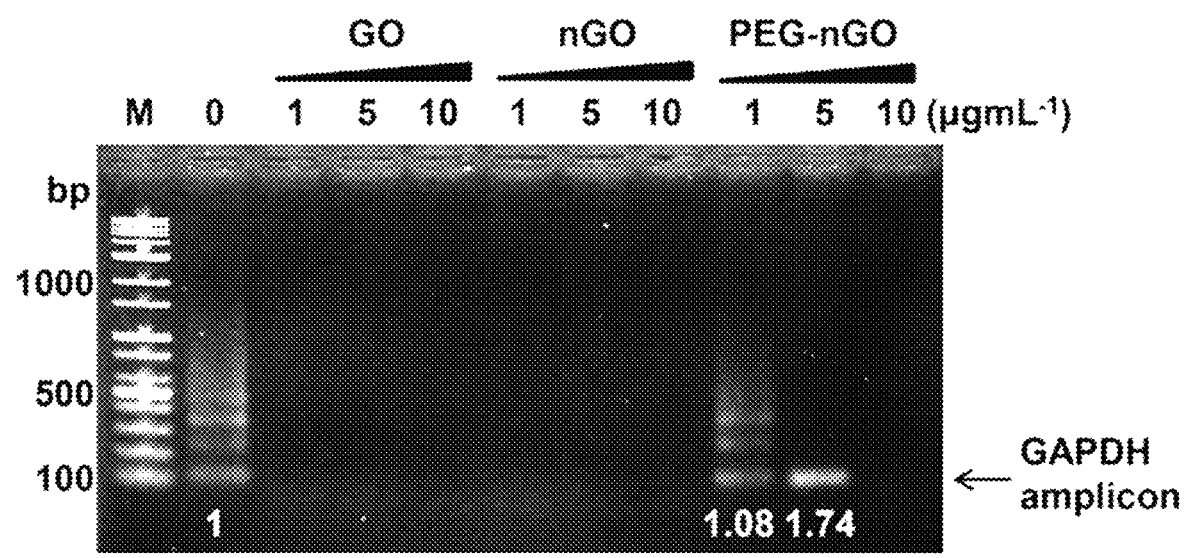
FIGS. 3A-3D includes images and a graph showing the results for confirming an increase in PCR efficiency when PEG-nGO was added to samples.
Figure 3B:
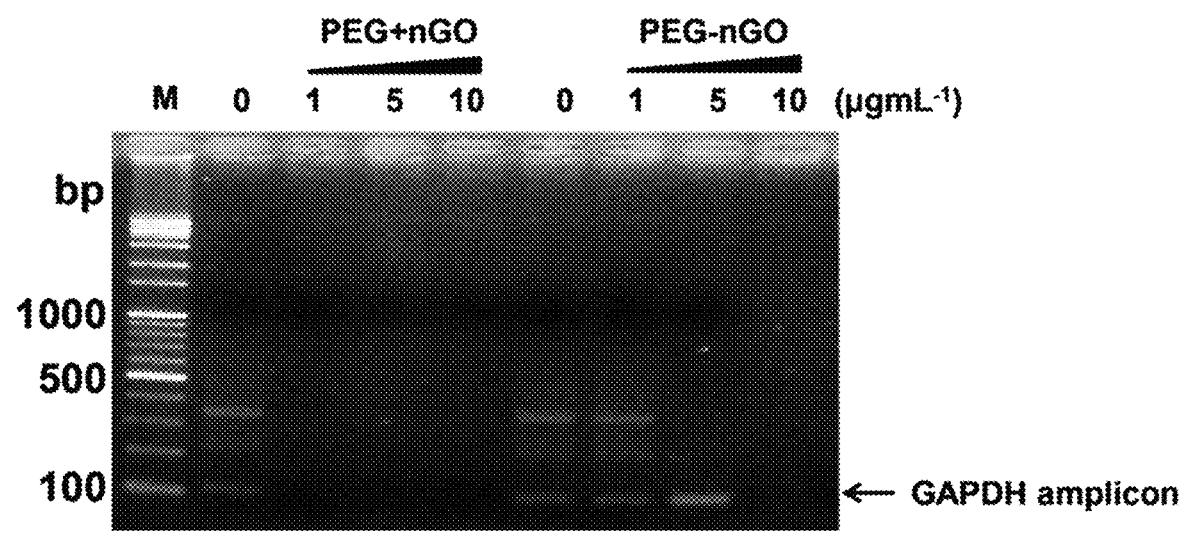
Figure 3C:
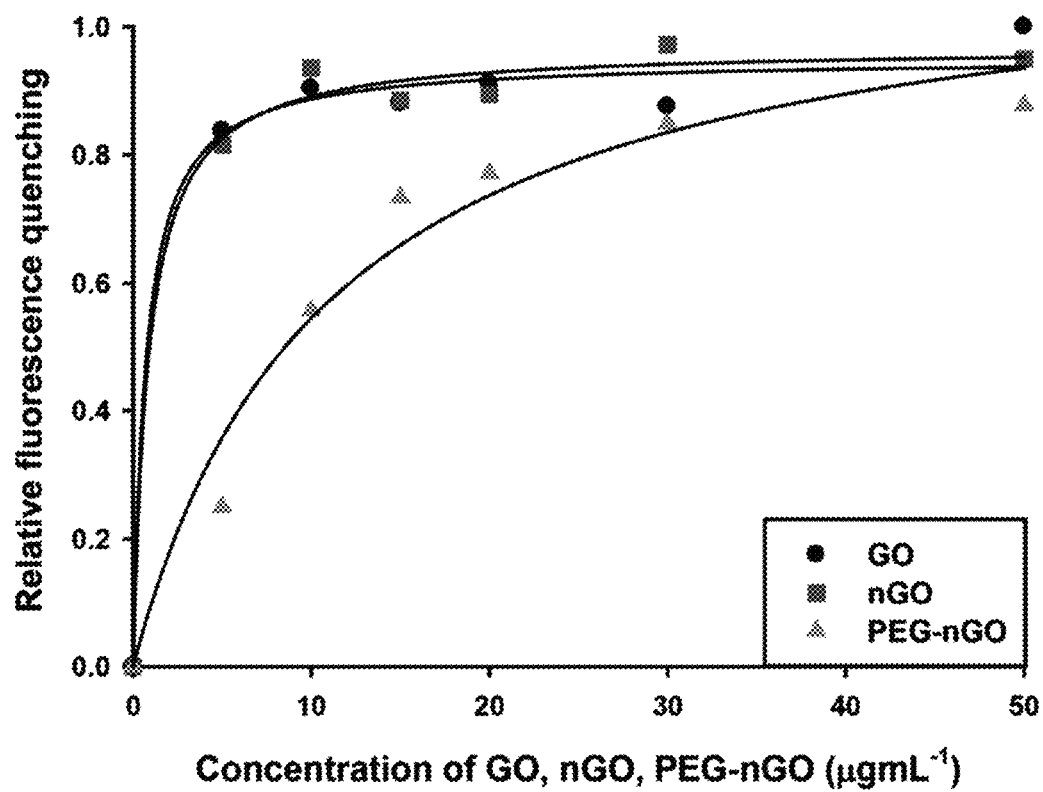
Figure 3D:
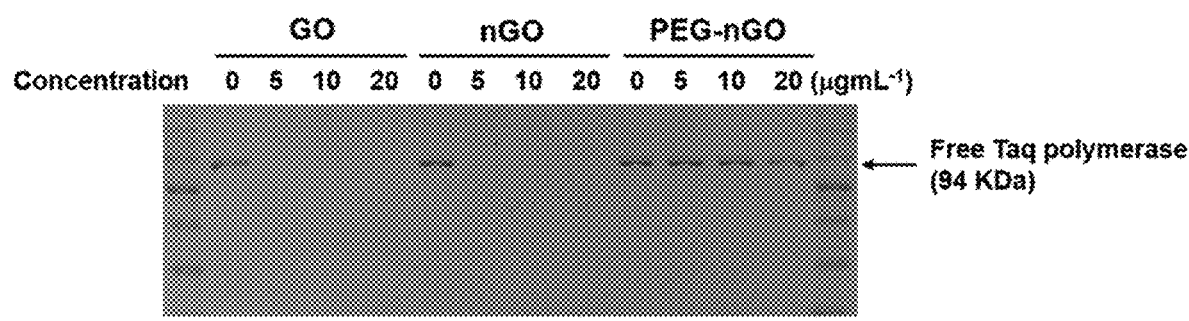

In addition, when PCR was performed on a PCR sample containing GO, nGO or PEG-nGO, a specific PCR product was not observed in a sample containing the GO or the nGO, whereas a specific PCR product was observed in a sample containing the PEG-nGO (FIG. 3A). It was confirmed that these results were obtained due to the bonding between PEG and nGO (FIG. 3B). In addition, it was confirmed that the PEG-nGO was effectively adsorbed to elements such as ssDNA and a DNA polymerase in a sample, resulting in the above results (FIGS. 3C and 3D).

Figure 4A:
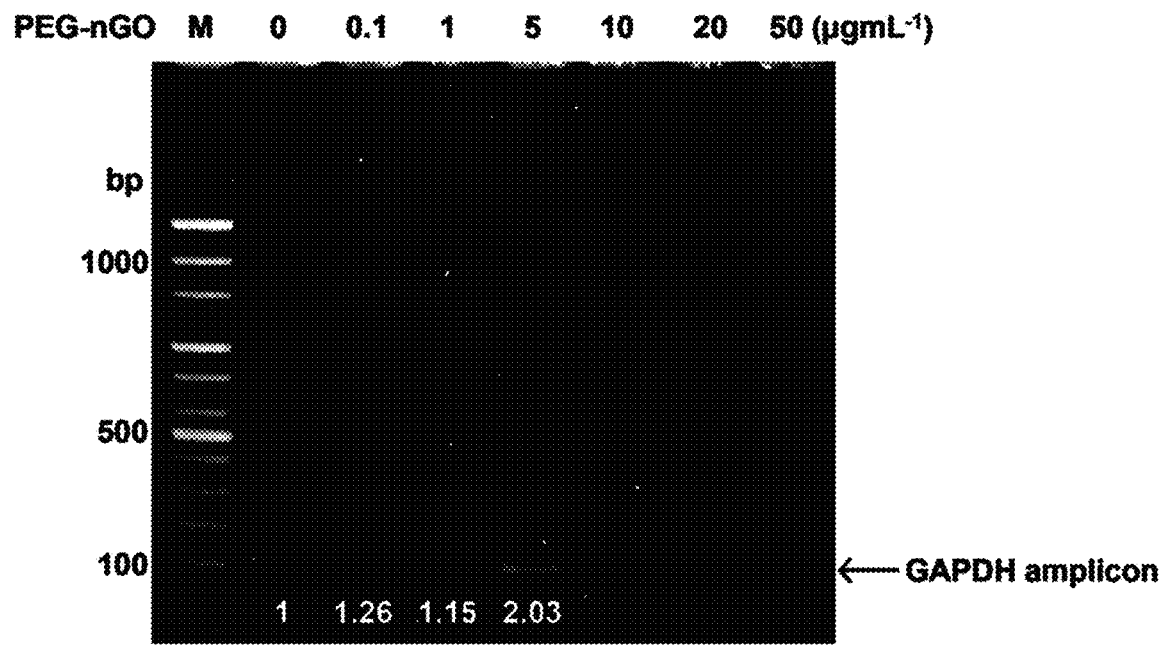
FIGS. 4A-4D includes images showing the results for confirming the optimal concentration of PEG-nGO required to increase the efficiency and specificity of PCR.
Figure 4B:
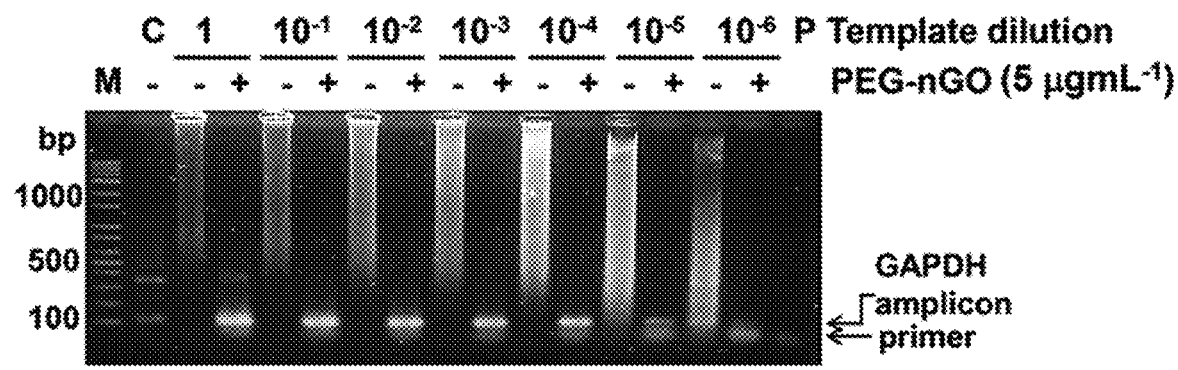
Figure 4C:
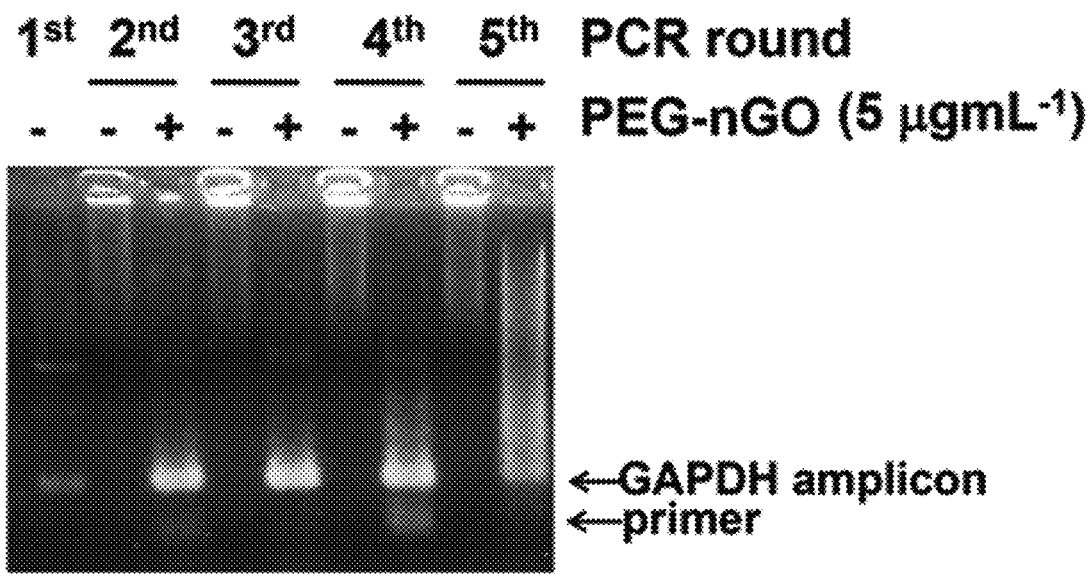
Figure 4D:
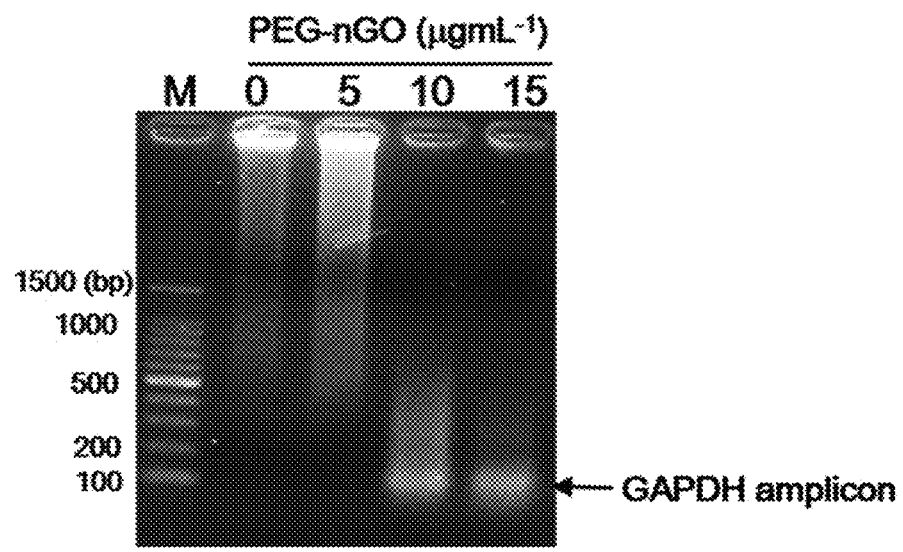

In addition, the present inventors confirmed the optimal concentration of the PEG-nGO for increasing the efficiency and specificity of PCR. As a result, the optimal concentration of the PEG-nGO was determined to be 5 μg/ml (FIG. 4A). To more specifically confirm the role of PEG-nGO in increasing the efficiency and specificity of PCR in consecutive rounds of PCR, PCR was performed by varying the conditions of PEG-nGO addition. It was confirmed that the PEG-nGO was adsorbed to primers and single-stranded DNA templates during PCR amplification, so that formation of primer dimers and reannealing of amplified DNA were reduced (FIGS. 4B to 4D).

Figure 5A:
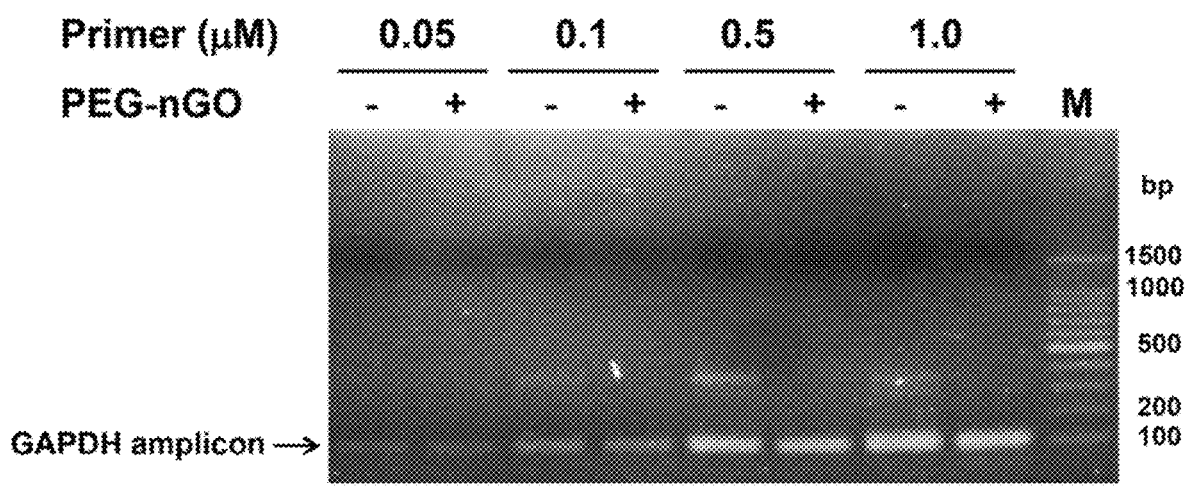
FIGS. 5A-5B includes images showing results confirming that PEG-nGO increases the efficiency and specificity of PCR by adsorbing to primers.
Figure 5B:
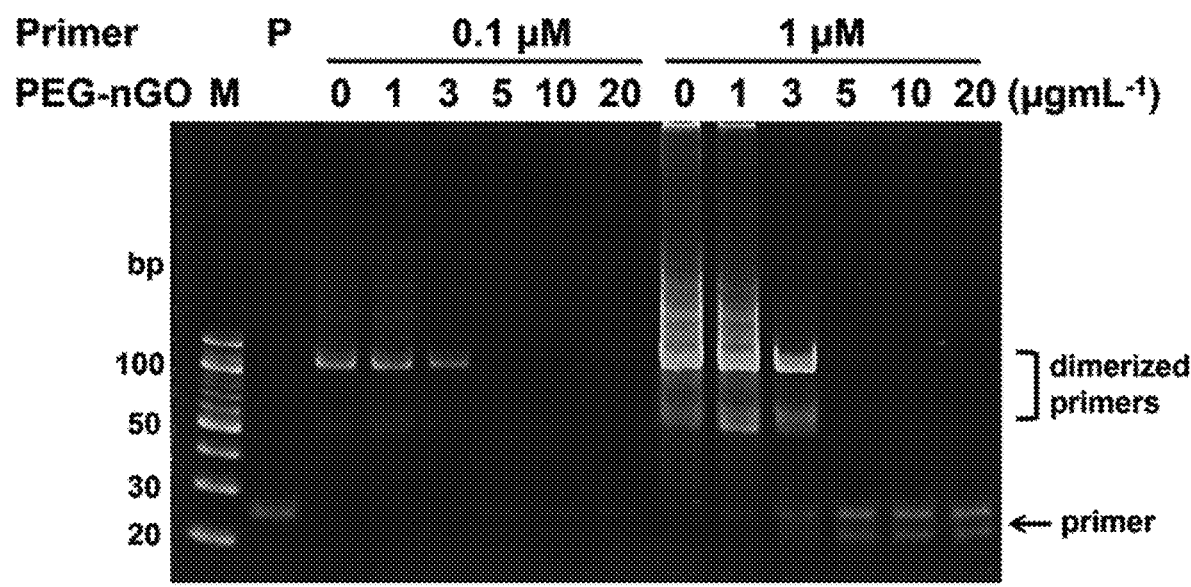

In addition, the present inventors predicted that the PEG-nGO inhibited dimerization of primers abundant in a sample in the initial stage of PCR. Thus, the effect of the PEG-nGO on PCR efficiency depending on the concentration of primers was confirmed. As a result, when performing conventional PCR by adding the PEG-nGO, the optimal concentration of the PEG-nGO was 5 μg/ml. At this concentration, the PEG-nGO was effectively adsorbed to primers and inhibited the generation of primer dimers (FIGS. 5A and 5B).

Figure 6:
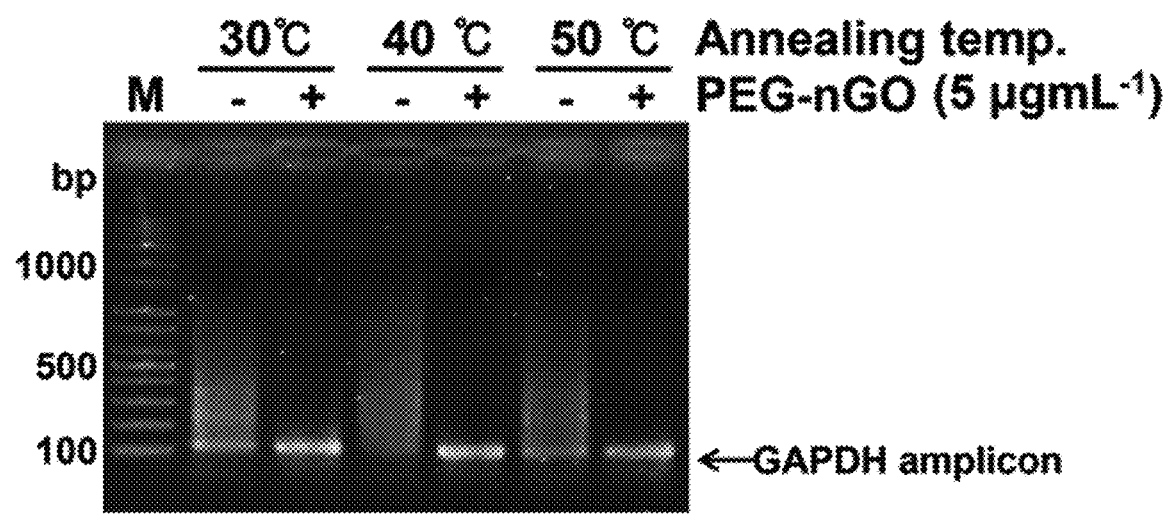
FIG. 6 is an image showing the result for confirming the effect of PEG-nGO on the efficiency and specificity of PCR depending on annealing temperature.

In addition, the present inventors confirmed whether smearing of a nonspecific DNA band was reduced depending on the presence or absence of the PEG-nGO even at a low annealing temperature. As a result, the PEG-nGO was adsorbed to ssDNA abundant in a PCR sample, so that the concentration of ssDNA was appropriately maintained while temperature was changed, thereby reducing erroneous binding between primers and DNA templates (FIG. 6).

In addition, the present inventors predicted that the PEG-nGO increased the specificity and efficiency of PCR by inhibiting reannealing of amplified DNA during the annealing step and promoted DNA melting during the denaturation step. As a result of conducting experiments to confirm the above prediction, it was confirmed that the PEG-nGO effectively inhibited the nonspecific reannealing of amplified DNA amplicons (FIG. 7A) and promoted dissociation of double-stranded DNA amplicons into single-stranded DNA amplicons, thereby reducing the time required for the denaturation step of PCR (FIGS. 7B and 7C).

Figure 8A:
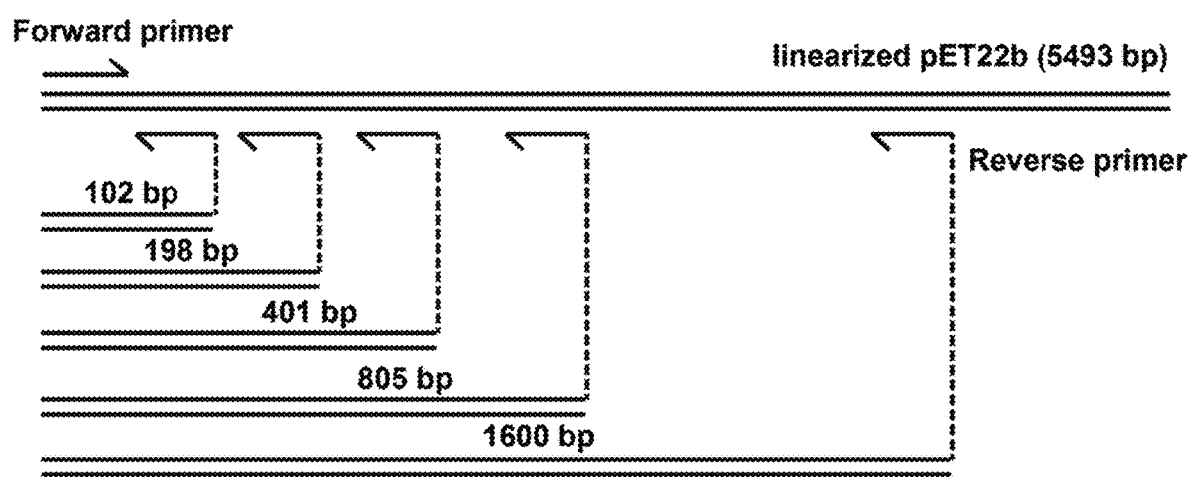
FIGS. 8A-8D includes a schematic view and images showing the results for confirming the effect of PEG-nGO on the efficiency and specificity of PCR according to a change in length of target DNA.
Figure 8B:
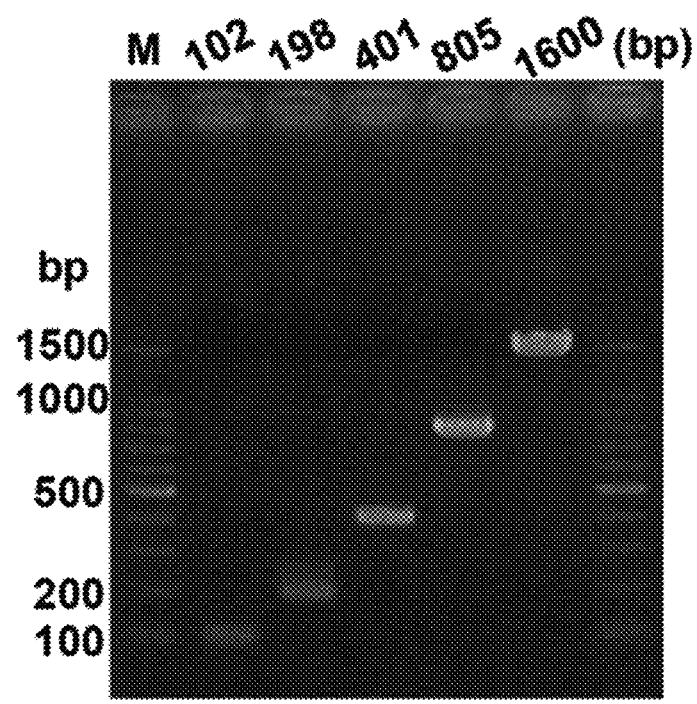
Figure 8C:
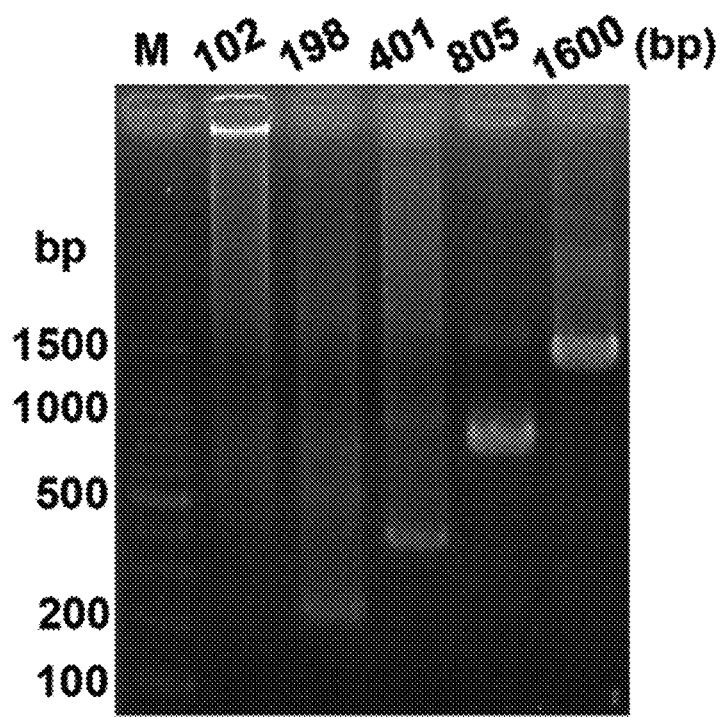

In addition, the present inventors confirmed whether PCR using the PEG-nGO was affected by the sequence size of target DNA. As a result, it was confirmed that, when the PEG-nGO was added to a PCR sample according to optimal conditions, the specificity and efficiency of PCR were improved regardless of the sequence size of the target DNA (FIGS. 8A to 8C).

The PEG-nGO of the present invention acts as intracellular SSBs, and may bind to single-stranded DNA resulting from the denaturation of double-stranded DNA and may protect the single-stranded DNA. Since the PEG-nGO is adsorbed to primers abundant in the early stage of PCR, formation of primer dimers and nonspecific annealing between the primers and DNA templates may be reduced. In addition, in the late stage of PCR, in which amplified PCR products are accumulated, the PEG-nGO effectively binds to single-stranded DNA resulting from the denaturation of double-stranded DNA and may inhibit reannealing of amplified ssDNA, thereby promoting annealing between primers and DNA templates.

Therefore, the PEG-nGO of the present invention i) may increase the efficiency and specificity of PCR even in PCR proceeding in multiple rounds; ii) may improve PCR efficiency by inhibiting formation of primer dimers in a sample and improper annealing of primers at low annealing temperatures; iii) may reduce the time required for the denaturation step during PCR by promoting separation of double-stranded DNA templates, thereby effectively providing DNA templates and reducing the overall PCR run time; and iv) may also improve PCR efficiency in PCR for amplifying genes having various sizes. Thus, when using the PEG-nGO, the disadvantages that may occur in conventional PCR techniques may be overcome, and the efficiency and specificity of PCR may be improved.

In addition, the present invention provides a method of performing PCR, the method including the following steps i) and ii):

i) a step of preparing a PCR sample by mixing a DNA template, dNTPs, a DNA polymerase, and forward and reverse primers for amplifying a target sequence with the composition for PCR of the present invention including PEG-nGO; and ii) a step of performing PCR using the prepared PCR sample.

The PEG-nGO of step i) is preferably present at a concentration of 1 to 10 μg/ml. When the PEG-nGO is contained in a sample at a concentration of less than 1 μg/ml, nonspecific DNA may be amplified because the PEG-nGO may not be effectively adsorbed to primers or ssDNA. When the PEG-nGO is contained in a sample at a concentration exceeding 10 μg/ml, since the PEG-nGO is strongly adsorbed to DNA, there is a lack of primers and DNA templates used for DNA amplification, so that DNA amplification products may not be significantly obtained. In view of the present invention in which the PEG-nGO is used to increase the efficiency and specificity of PCR compared to conventional PCR techniques, the PEG-nGO is most preferably present at a concentration of 5 μg/ml in a sample, without being limited thereto. The concentration of the PEG-nGO may be experimentally determined by a typical technician. That is, when PCR products are subjected to agarose gel electrophoresis and a single DNA band is observed, it may be judged that the concentration of the PEG-nGO used in PCR is appropriate.

Each forward and reverse primer of step i) is present at a concentration of 0.1 to 1.0 μM, without being limited thereto, the concentration of the primers may be experimentally determined by a typical technician. That is, when PCR products are subjected to agarose gel electrophoresis and a single DNA band is observed, it may be judged that the concentration of the primers used in PCR is appropriate.

In step ii), PCR may be selected from the group consisting of quantitative PCR (qPCR), real-time PCR, reverse transcription PCR (RT-PCR), solid phase PCR, competitive PCR, overlap-extension PCR, multiplex PCR, nested PCR, inverse PCR, ligation-mediated PCR, intersequence-specific PCR (ISSR), methylation-specific PCR (MSP), colony PCR, miniprimer PCR, nanoparticle-assisted PCR (nanoPCR), thermal asymmetric interlaced PCR (TAIL-PCR), touchdown PCR (step-down PCR), hot start PCR, in-silico PCR, allele-specific PCR, assembly PCR, asymmetric PCR, dial-out PCR, digital PCR (dPCR), and helicase-dependent amplification. The PCR method of the present invention may be applied without limitation, when PCR is performed by a typical technician to artificially amplify DNA.

Hereinafter, the present invention will be described in more detail with reference to Examples. It will be apparent to those skilled in the art that these embodiments are for illustrative purposes only and that the scope of the present invention is not construed as being limited by these examples.

EXAMPLES

Example 1. Preparation of Polyethylene Glycol-Engrafted Nano-Sized Graphene Oxide (PEG-nGO)

PEG-nGO for use in the present invention was prepared.

Specifically, GO (HCGO-W-175) was purchased from Graphene Laboratories Co. (Ronkonkoma, N.Y., USA). A 6-arm polyethylene glycol amine (15 kDa) was purchased from SunBio Co. (Seoul, Korea). The GO having a concentration of 5 mg/ml was diluted to a concentration of 2 mg/ml, and then subjected to tip ultrasonication on ice for 5 hours to prepare GO that is broken up in nano units (i.e., nano-sized GO, nGO). Then, for PEGylation, 1.2 g of NaOH and 1.0 g of chloroacetic acid were added to 5 ml of the prepared nGO suspension, followed by ultrasonication for 4.5 hours. This allows the —OH of the surface of the nGO to be converted to a —COOH group through conjugation of an acetic acid moiety to obtain nGO (HOOC-nGO) having a carboxyl group bonded thereto. The obtained HOOC-nGO solution was repeatedly rinsed with distilled water for neutralization and then filtered through a 0.2 µm filter membrane (Millipore, USA) to obtain purified HOOC-nGO. The purified HOOC-nGO was diluted with water until an optical density was 0.4 at 808 nm. Then, 2 mg/ml of the 6-arm PEG-amine solution was added to the diluted HOOC-nGO solution and they were mixed using ultrasonic waves for 5 minutes. Thereafter, N-(3-dimethylaminopropyl)-N'-ethyl-carbodiimide hydrochloride was added to the mixed solution so that the final concentration was 5 mM, and the mixture was stirred for 12 hours. The mixing reaction was terminated by addition of 50 mM mercaptoethanol. The obtained mixture was diluted in distilled water for 12 hours, centrifuged at 10,000×g for 1 hour in phosphate-buffered saline to obtain a supernatant containing PEG-nGO, and the supernatant was stored at 4° C.

Figure 2A:
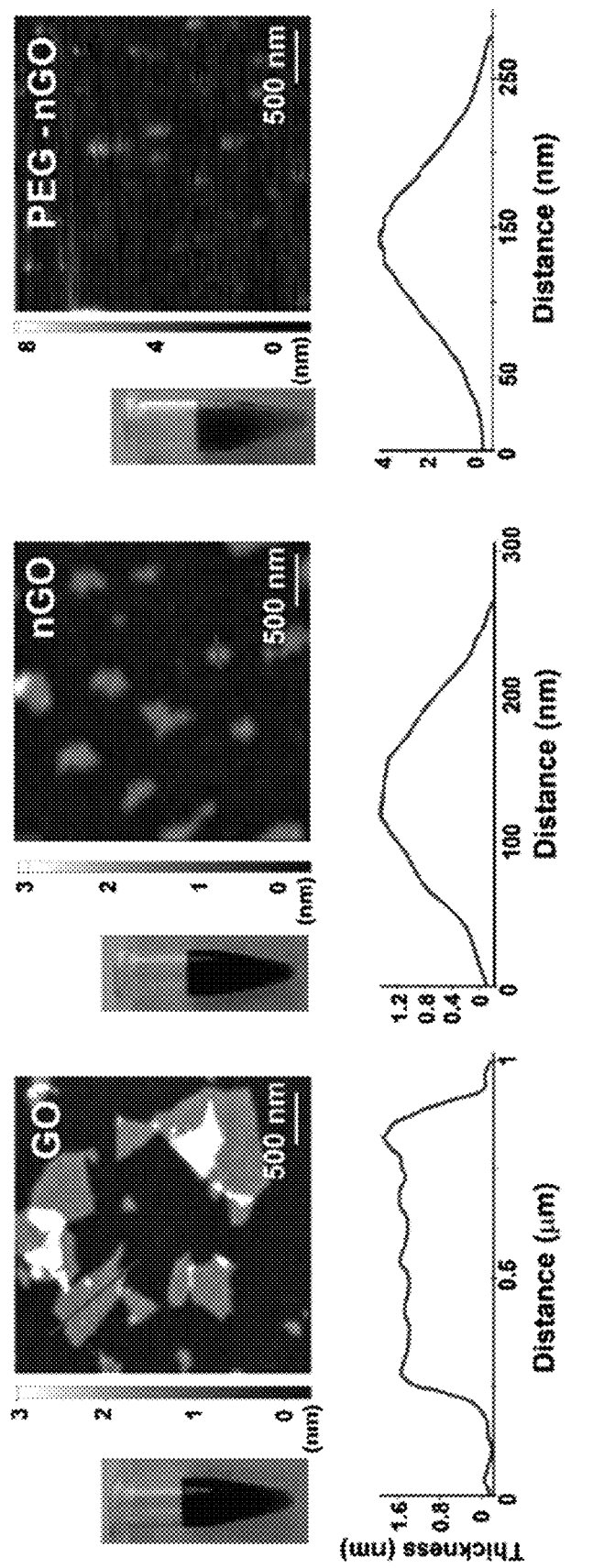
FIGS. 2A-2B includes diagrams showing the results for confirming characteristics of PEG-nGO.
Figure 2B:
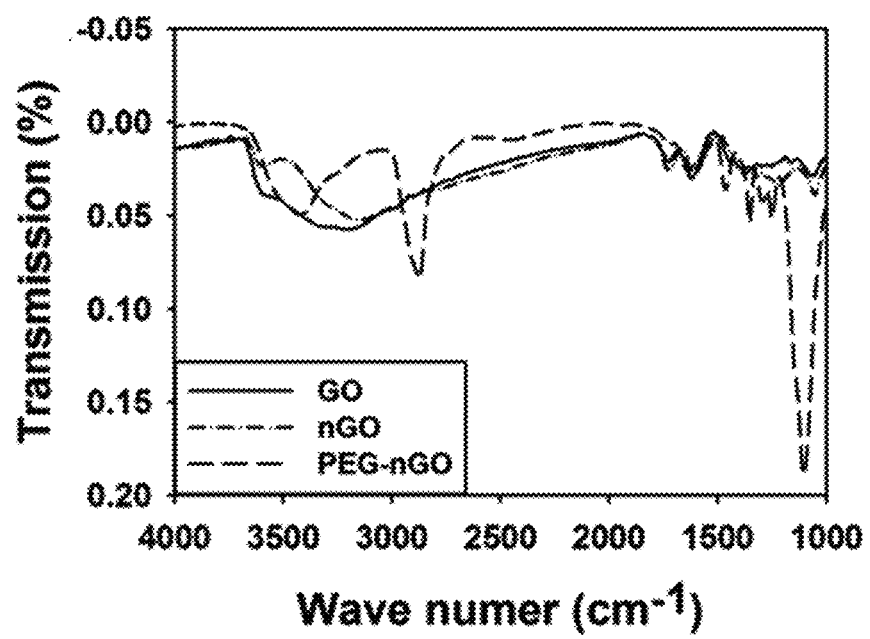

The prepared graphene materials (GO, nGO, and PEG-nGO) were analyzed using atomic force microscopy (XE-100 AFM; ParkSystems, Seoul, Korea) and Fourier transform infrared spectroscopy (Tensor 27 FT-IR spectrometer; Bruker, Billerica, Mass., USA). As a result, as shown in FIG. 2A, according to AFM analysis, the GO particles exhibited a broad particle distribution of 400 to 1,000 nm, whereas the diameters of the nGO and PEG-nGO particles were as small as about 200 nm. That is, the nGO and PEG-nGO particles had a uniform particle size compared to the GO particles (FIG. 2A). In addition, as a result of FT-IR spectrum analysis, the thicknesses of the GO and the nGO were about 1.2 to 1.6 nm, and it was confirmed that a single layer of graphene was formed (FIG. 2B). In contrast, the thickness of the PEG-nGO was 4 to 5 nm due to the binding of PEG to the surface of nGO (FIG. 2B). According to the spectrum of the PEG-nGO, a new amide carbonyl group was formed near ~1650 $cm^{-1}$ and a methylene bond was formed near ~2,800 $cm^{-1}$, as compared with the FT-IR spectrum of the GO and the nGO.

Example 2. Evaluation of PCR Efficiency in Samples Containing PEG-nGO

<2-1> Evaluation of Effect of Addition of GO, nGO or PEG-nGO on PCR Efficiency

To confirm whether PCR efficiency was increased when the PEG-nGO of the present invention was added, PCR amplification was performed on a PCR sample to which GO, nGO or the PEG-nGO was added.

Specifically, first, intracellular RNA was extracted from a human leukemia cell line, K562 (purchased from ATCC) using a TRIzol® reagent (Invitrogen Co., USA). 1 µg of the extracted RNA was used as a template, and reverse transcription-polymerase chain reaction (RT-PCR) was performed using a PrimeScript™ 1st strand cDNA synthesis kit (TaKaRa Bio Co., Shiga, Japan) to obtain cDNA. The cDNA complementary to cell-derived RNA was stored at −20° C. for future use.

The cDNA was used as a DNA template, and GAPDH (110 bp) was selected as a target sequence to be amplified. Primers for amplifying GAPDH were synthesized and purified by Cosmo Genetech Co. (Seoul, Korea). A forward primer is represented by SEQ ID NO: 1 (5'-TTG TTG CCA TCA ATGACC CCT TCA TTG ACC-3'), and a reverse primer is represented by SEQ ID NO: 2 (5'-CTT CCC GTT CTC AGC CTT GACGGT G-3'). A PCR sample was prepared by mixing 3 µl (150 ng) of cDNA, 0.083 U/µl Ex Taq® polymerase (TaKaRa Bio Co., Shiga, Japan), 0.25 mM deoxynucleotides (dNTPs), 1×Ex Taq® buffer, 100 nM of each PCR primer, and PEG-nGO (at a concentration of 1, 5 or 10 µg/ml), and the total volume of the PCR sample was adjusted to 30 µl. PCR amplification was performed according to the following repetition program: after pre-denaturation at 95° C. for 5 minutes, a reaction cycle composed of a denaturation step at 95° C. for 30 seconds, an annealing step at 60° C. for 30 seconds, and an extension step at 72° C. for 1 minute was repeated 30 times, and a final step was conducted at 72° C. for 8 minutes. The PCR products were separated by agarose gel electrophoresis and identified as DNA bands stained with EtBR. The intensity of the DNA band was quantitatively analyzed using ImageJ software (http://rsb.info.nih.gov/ij/index.html).

As a result, as shown in FIG. 3A, GAPDH amplicons were not detected in a sample containing the GO or the nGO, whereas cDNA amplification was not inhibited in a sample containing the PEG-nGO (FIG. 3A). For the sample containing the PEG-nGO, the patterns of cDNA bands were different depending on the concentration of the PEG-nGO. In GAPDH amplicons, nonspecific bands were observed in a sample containing the PEG-nGO at a concentration of 1 µg/ml, but only one specific band was observed in a sample containing the PEG-nGO at a concentration of 5 µg/ml. However, when the PEG-nGO was contained in a PCR sample at high concentration (e.g., 10 µg/ml), PCR was inhibited.

<2-2> Evaluation of Effect of PEG and nGO Binding on PCR Efficiency in Sample

The above results show that PCR efficiency is increased when the PEG-nGO is added compared to when the GO or the nGO is added. It was further confirmed that this effect was due to the PEG-nGO, a conjugated form of PEG and the nGO.

Specifically, when PCR samples were prepared, the PEG-nGO was mixed at a concentration of 1, 5 or 10 µg/ml (PEG-nGO) or each of PEG and nGO was mixed at a concentration of 1, 5 or 10 µg/ml (PEG+nGO). PCR for amplification of GAPDH cDNA was performed in the same manner as in <2-1> above.

As a result, as shown in FIG. 3B, in a sample containing the PEG-nGO at a concentration of 5 µg/ml, a single band was observed due to specific binding, whereas no PCR amplification was observed in the cases of PEG+nGO (FIG. 3B). These results show that when the PEG-nGO is contained in a sample at an optimal concentration, PCR specificity may be increased and a single amplicon may be generated.

<2-3> Confirmation of Affinity Between PEG-nGO and PCR Elements

To further clarify a mechanism by which PCR efficiency is increased when the PEG-nGO is included in a PCR sample, binding affinity between the PEG-nGO and PCR elements, such as ssDNA and a DNA polymerase, was confirmed.

Specifically, first, to confirm binding affinity between nGO materials (GO, nGO or PEG-nGO) and ssDNA, 10 nM fluorescein isothiocyanate (FITP)-labeled 95 mer ssDNA was mixed with various concentrations of the GO, the nGO or the PEG-nGO (0, 1, 5, 10, 15, 20, 30, 40, and 50 μg/ml) and heated at 95° C. for 10 minutes. Thereafter, the reaction mixtures were transferred to a 96-well plate, and fluorescence intensity was measured at wavelengths of $\lambda_{ex}$=485 nm and $\lambda_{em}$=535 nm using a multilabel plate reader (VICTOR X3®; PerkinElmer, Waltham, Mass., USA). Fluorescence intensity was calculated by the equation $(F_{max}-F)/(F_{max}-F_{min})$ ($F_{max}$ and $F_{min}$ represent the maximum and minimum absorbance values, respectively). The binding affinity Kd value indicates the affinity between ssDNA and the graphene materials, and was calculated by applying the fluorescence intensity to the hyperbolic equation.

Next, to confirm binding affinity between nGO materials (GO, nGO or PEG-nGO) and a DNA polymerase, Taq DNA polymerase (0.2 μg/μl) was mixed with various concentrations of the GO, the nGO or the PEG-nGO (0, 5, 10 and 20 μg/ml) and heated at 95° C. for 10 minutes. The heated mixtures were loaded on an 8% SDS-PAGE gel and analysis was performed.

As a result, as shown in FIG. 3C, Kd values indicating the interaction between each of the GO, the nGO, and the PEG-nGO and ssDNA were 0.71, 0.87, and 10.93 μg/ml, respectively. Based on this result, it was confirmed that the PEG-nGO showed lower affinity to ssDNA than the GO or the nGO (FIG. 3C). In addition, as shown in FIG. 3D, at concentrations used for PCR, Taq DNA polymerase was adsorbed to the GO or the nGO, whereas Taq DNA polymerase was not adsorbed to the surface of the PEG-nGO (FIG. 3D). These results show that the PEG-nGO exhibits lower affinity to ssDNA or a DNA polymerase than the GO and the nGO. That is, the PEG-nGO exhibited an affinity suitable for use in PCR. ssDNA and Taq DNA polymerase were adsorbed to the surfaces of the GO and the nGO with strong affinity, so that DNA amplification was inhibited.

Example 3. Establishment of Optimal Conditions for PEG-nGO Addition to Increase PCR Efficiency and Specificity <3-1> Determination of Optimal Concentration of PEG-nGO To determine the optimal concentration of the PEG-nGO for increasing PCR specificity, PCR amplification was performed on samples containing various concentrations of the PEG-nGO.

Specifically, a PCR sample was prepared by mixing 3 μl (150 ng) of cDNA, 0.083 U/μl Ex Taq® polymerase, 0.25 mM deoxynucleotides (dNTPs), 1×Ex Taq® buffer, and 100 nM of each PCR primer, and various concentrations of the PEG-nGO (0, 0.1, 1, 5, 10, 20, and 50 μg/ml) were added to the sample, respectively, and the total volume of the sample was adjusted to 30 μl. The prepared PCR samples were subjected to PCR under the same conditions as Example <2-1> to amplify GAPDH cDNA, and electrophoresis was performed to detect DNA bands.

As a result, as shown in FIG. 4A, nonspecific bands were observed as the concentration of the PEG-nGO added to the sample increased from 0 to 1 μg/ml, and no PCR band was observed in the samples containing the PEG-nGO at an excessive concentration of 10 μg/ml or more (FIG. 4A). Thus, it was determined that the optimal concentration of PEG-nGO was 5 μg/ml. Since about 30% of ssDNA was adsorbed to 5 μg/ml of the PEG-nGO (FIG. 3C), the PEG-nGO was adsorbed to primers and single-stranded DNA templates during PCR amplification, thereby reducing formation of primer dimers and reannealing of amplified DNA.

<3-2> Evaluation of Effect of PEG-nGO Addition on PCR Efficiency in Consecutive Rounds of PCR A large number of nonspecific amplicons may be generated due to nonspecific binding of primers or the like during PCR. To solve this problem, various PCR techniques such as nested PCR may be used. In nested PCR, PCR amplification is performed in two separate steps. In the first step, a primer set for amplifying a broad range including a target sequence on a DNA template is used, and in the second step, primer sequences for amplifying only the target sequence are generally used as an inner primer set. Thus, nested PCR has a disadvantage that gene amplification reaction should be performed in two steps using different primer sets.

To confirm the effect of the PEG-nGO in increasing the efficiency and specificity of the PCR proceeding in a continuous process, in the first and second steps, PCR was performed depending on whether the PEG-nGO was added. Specifically, a PCR sample with or without 5 μg/ml of the PEG-nGO was prepared, and the first round of PCR was performed. The PCR products obtained from the first round of PCR were subjected to a serial dilution ($10^0$ to $10^{-6}$ times), and the second round of PCR was performed on the diluted PCR products. After completion of PCR, electrophoresis was performed to identify DNA bands.

As a result, as shown in FIG. 3B, when a total of 2 PCR steps were performed on PEG-nGO-added samples, bands corresponding to individual target DNA were observed without band smearing. When the second round of PCR was performed on the first round of PCR products, which were serially diluted, a clear single DNA band was observed in all samples (FIG. 4B). However, when the PEG-nGO was not added, nonspecific bands were observed in all samples as a result of electrophoresis, indicating that nonspecific PCR products were generated (FIG. 4B). These results indicate that the PEG-nGO may increase the specificity and efficiency of PCR in the second round of PCR performed with primers used in the first round of PCR. Therefore, it was confirmed that nested PCR performed in separate steps may not be required for performing PCR by adding the PEG-nGO.

In addition, to determine whether the efficiency of DNA amplification may be increased when consecutive rounds of PCR using the same PCR primers was performed in the presence of the PEG-nGO, consecutive rounds of PCR was performed on samples containing the PEG-nGO, and amplification of target DNA was monitored. At this time, PCR was repeatedly performed for a total of five rounds. After each step, PCR products were directly used in the next step as a DNA template without dilution.

As a result, as shown in FIG. 4C, in samples without the PEG-nGO, smearing of a DNA band due to nonspecific DNA amplification was observed in all PCR rounds, whereas nonspecific DNA amplification was decreased in samples containing the PEG-nGO, and a single DNA band was generated as PCR proceeded from the second round to the fourth round (FIG. 4C). However, PCR specificity was reduced in the fifth round. These results suggested that, during repetitive PCR, the amount of PCR amplicons was highly increased compared with DNA templates added at the early stage of PCR. Therefore, an experiment in which a high concentration of the PEG-nGO was added was conducted later.

Since it is necessary to add the PEG-nGO in the fifth round, in the first to fourth rounds, PCR was performed under the same conditions, and the fifth round of PCR was performed under conditions in which the concentration of the PEG-nGO was increased (0, 5, 10 or 15 µg/ml).

As a result, as shown in FIG. 4D, it was confirmed that specific PCR amplification was possible even after the fifth round in a sample to which 15 µg/ml of the PEG-nGO was added (FIG. 4D). Therefore, it was confirmed that when ssDNA denatured by heat in repeated PCR steps is increased in a sample, the PEG-nGO should be added at a high concentration to specifically amplify target DNA.

Example 4. Evaluation of Effect of Adsorption Between PEG-nGO and Primers on Efficiency and Specificity of PCR <4-1> Evaluation of Effect of PEG-nGO on PCR Efficiency at Various Primer Concentrations To determine whether the optimal concentration of the PEG-nGO varies with an initial primer concentration, PCR was performed by adding PEG-nGO at a concentration of 5 µg/ml and adding primers at various concentrations (0.05, 0.1, 0.5 or 1.0 µM).

As a result, as shown in FIG. 5A, when primers were added at the lowest concentration of 0.05 µM, DNA was significantly not amplified, so that a PCR band was not observed after electrophoresis. In the case of PCR samples containing primers at a concentration of 0.1 to 1.0 µM, when the PEG-nGO was not added, nonspecific DNA bands due to nonspecific PCR amplification were observed (FIG. 5A). On the other hand, when the PEG-nGO was added, as the concentration of primers increased from 0.1 to 1.0 µM, amplification of nonspecific DNA gradually decreased and a single band was observed after electrophoresis (FIG. 5A).

These results indicate that it is advantageous to perform PCR by adding the PEG-nGO at an optimal concentration (5 µg/ml) that may be selected when performing conventional PCR. This indicates that the PEG-nGO may increase the specificity of DNA amplification in a broad range of primer concentrations, including a low concentration at which the PEG-nGO is not required.

<4-2> Determination of Adsorption Between PEG-nGO and Primers in Sample not Containing DNA Template In conventional PCR methods, non-specific PCR products may be generated by interaction between primers, resulting in primer dimerization. Primer dimers may be generated when primer concentration is high or the 3'-ends of forward and reverse primers are complementary to each other. Based on the fact that the PEG-nGO is adsorbed to ssDNA in a concentration-dependent manner, as shown in Example <2-3> (FIG. 3C), it was predicted that the PEG-nGO may be adsorbed to primers contained at an excessive amount to inhibit formation of primer dimers. To confirm this hypothesis, a PCR sample containing primers for GAPDH cDNA amplification but no DNA template was prepared, and PCR amplification was performed.

As a result, as shown in FIG. 5B, in samples not containing a target DNA template, DNA amplification products were not generated due to primer dimerization. However, primer dimer formation and amplification thereof were significantly reduced with increasing the concentration of the PEG-nGO (FIG. 5B). Bands corresponding to amplified primer dimers were not observed in a sample containing 5 µg/ml of the PEG-nGO. Thus, it was confirmed that, even in conventional PCR, the PEG-nGO was adsorbed to primers added in an excessive amount in the first step, thereby inhibiting primer dimer formation according to temperature change during a PCR process.

Example 5. Evaluation of Effect of PEG-nGO on Efficiency and Specificity of PCR at Various Annealing Temperatures Since primers may easily bind to DNA template strands at low temperatures, the yield of PCR products may be increased, but the specificity of DNA amplification may be reduced. Thus, to confirm whether a smearing phenomenon due to nonspecifically amplified DNA may be reduced depending on the presence or absence of the PEG-nGO even at low annealing temperatures, DNA was amplified under PCR conditions in which an annealing temperature was set at 30 to 50° C.

As a result, as shown in FIG. 6, nonspecific bands were not observed in samples to which the PEG-nGO was added (FIG. 6). These results indicate that the PEG-nGO is adsorbed to ssDNA contained in a large amount in a PCR sample, so that the concentration of ssDNA is appropriately maintained during temperature changes. That is, the PEG-nGO may reduce improper binding between primers and DNA templates.

Example 6. Evaluation of Effect of PEG-nGO on Reannealing of DNA Templates Denatured by Temperature The accuracy of DNA replication is a very important factor in DNA amplification. While DNA is amplified in the cells, double-stranded DNA (dsDNA) is separated by a DNA helicase, and various SSBs bind to the separated ssDNA. At this time, SSBs inhibit reannealing of ssDNA, thereby ensuring high accuracy and efficiency in DNA replication. In the present invention, the PEG-nGO was expected to play a role similar to SSBs. Thus, the present inventors expected that the PEG-nGO may increase PCR specificity and efficiency by inhibiting reannealing of amplified DNA during the annealing step, and may promote DNA melting during the denaturation step.

<6-1> Determine Whether PEG-nGO Protects ssDNA in Consecutive Rounds of PCR

To prove this hypothesis, PCR samples with or without 1.0 µM of each primer were prepared and consecutive rounds of PCR were performed. At this time, no PEG-nGO was added in the first PCR round, and 3, 5 or 10 µg/ml of PEG-nGO was added in the second PCR round.

Figure 7A:
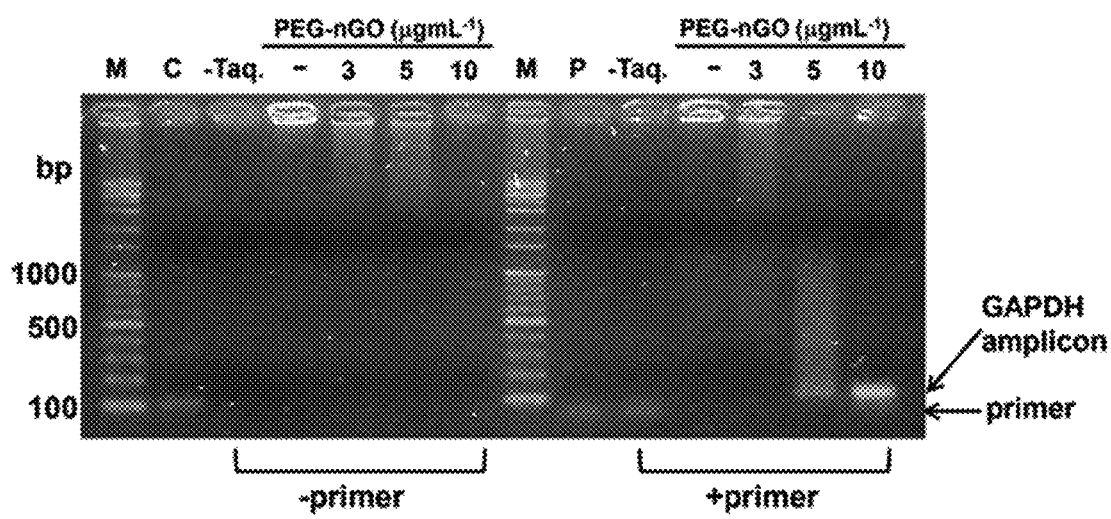
FIGS. 7A-7C includes images and graphs showing the results for confirming the effect of PEG-nGO inhibiting reannealing of DNA templates denatured by temperature.
Figure 7B:
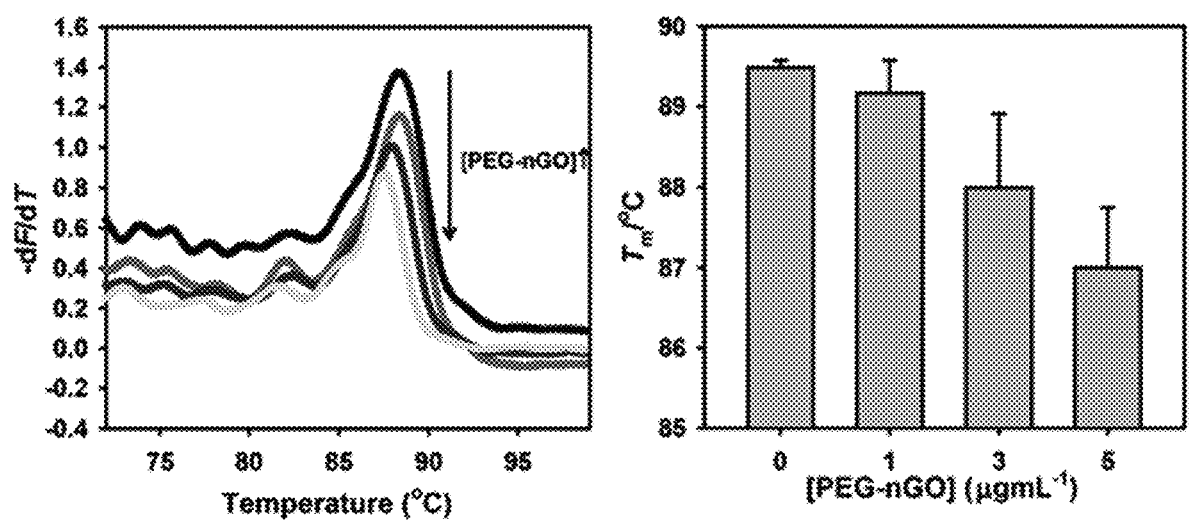
Figure 7C:
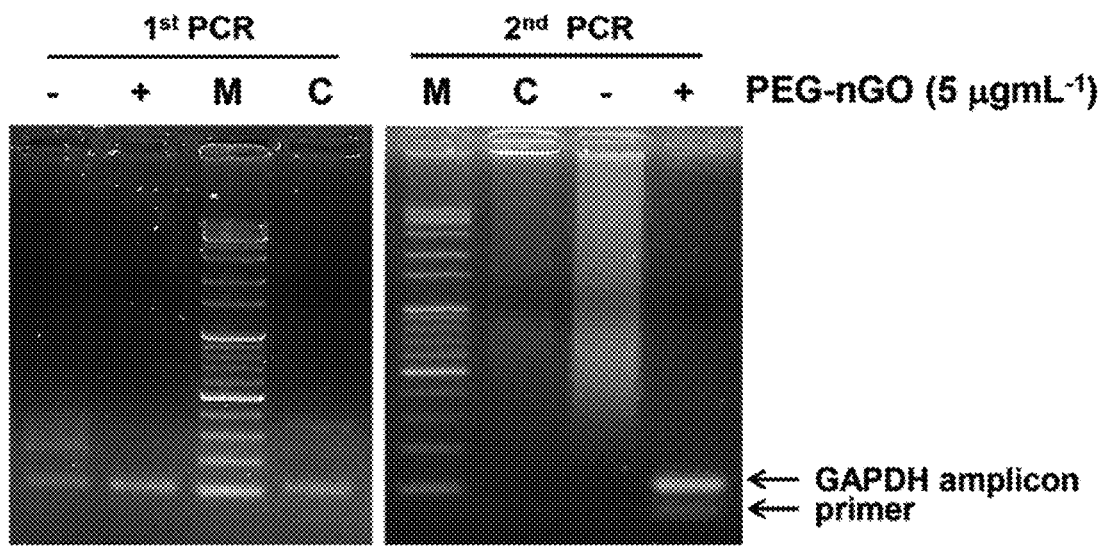

As a result, as shown in FIG. 7A, high-molecular-weight DNA was nonspecifically amplified in a sample without primers, which was the result of amplification of non-target sequences due to nonspecific binding of DNA templates present in a large amount in the sample (FIG. 7A). These nonspecific DNA bands decreased gradually with increasing concentrations of the PEG-nGO in a PCR sample, and no nonspecific DNA bands were observed when the PEG-nGO was added at a concentration of 10 µg/ml. However, in the case of a sample group to which primers were added, the second round of PCR was performed using a PCR sample containing 10 µg/ml PEG-nGO, and the obtained PCR products were electrophoresed, a band corresponding to amplified target DNA was observed (FIG. 7A). These results indicate that the PEG-nGO may suppress nonspecific reannealing of amplified DNA during PCR.

<6-2> Evaluation of Effect of PEG-nGO on DNA Melting

To determine the effect of temperature on the PEG-nGO in increasing PCR efficiency, the effect of the PEG-nGO on the melting temperature (Tm) of PCR products was confirmed by measuring the amount of dsDNA present in the bound state without ssDNA denaturation during PCR. 1×SYBR Green I (Invitrogen Co., Carlsbad, Calif., USA), 5 μl of 0.16 μg/μl 110-bp GAPDH amplicons, and the PEG-nGO (0, 1, 3, or 5 μg/ml) were mixed, and the final volume was adjusted to 20 μl. Thereafter, using a real-time gene amplifier (Rotor-Gene Q; Qiagen, Hilden, Germany), fluorescence changes were measured at wavelengths of $\lambda_{ex}$=470 nm and $\lambda_{em}$=510 nm at every 0.5° C. rise while raising the temperature from 25 to 99° C. Based on the obtained results, melting temperatures (Tm) were determined.

As a result, the melting curve of amplified dsDNA is shown in FIG. 7B. As the concentration of the PEG-nGO increased, Tm decreased. These results indicate that the PEG-nGO may promote dissociation of dsDNA.

<6-3> Evaluation of Effect of PEG-nGO on Dissociation of Amplified dsDNA

To confirm whether the PEG-nGO may facilitate dissociation of PCR-amplified dsDNA, a PCR cycle composed of three steps (denaturation, annealing, and extension steps) was shortened to two steps, that is, a PCR cycle composed of a first step at 95° C. for 1 second and a second step at 60° C. for 15 seconds was repeated 30 times. As a control group (C), a sample not containing the PEG-nGO was used. In this case, a PCR cycle composed of a first step at 95° C. for 30 seconds, a second step at 60° C. for 30 seconds, and a third step at 72° C. for 1 minute was repeated 30 times.

As a result, as shown in FIG. 7C, when the PEG-nGO was present in a sample, amplified DNA bands were clearly observed in the first and second rounds of PCR, and nonspecific DNA amplification was not observed. On the other hand, when PCR was performed on a sample not containing the PEG-nGO, nonspecific DNA amplification was observed at all rounds, and band smearing was observed in electrophoresis results (FIG. 7C). These results show that the cycle of temperature repetition may be made easier and faster because the PEG-nGO may facilitate the dissociation of PCR products in the form of dsDNA.

Example 7. Evaluation of Effect of PEG-nGO on Efficiency and Specificity of PCR Depending on Lengths of Target DNA To determine whether the PEG-nGO may increase PCR specificity when target DNA having various lengths was amplified, PCR was performed on target DNA sequences having various lengths as a DNA template. PCR to obtain DNA amplicons of various sizes was performed using pET22b(+) (Merck Millipore, Darmstadt, Germany), a linear plasmid DNA, as a template, and appropriate primers (shown in Table S1 and FIG. 6) were used. The linear DNA plasmid was cleaved by EcoRI at 37° C. for 1 hour, and the cleaved plasmid was obtained by ethanol precipitation. One forward primer and five reverse primers shown in Table 1 below were used in combination so that amplicons having lengths of 102, 198, 401, 805, and 1600 bp were amplified. As shown in FIG. 8A, PCR was performed to amplify the five kinds of amplicons. At this time, the obtained pET22b plasmid DNA was added as a template, and each forward and reverse primer was added to prepare a sample. Then, PCR was performed in two steps to amplify DNA with or without the PEG-nGO. After PCR, PCR bands were analyzed.

TABLE 1

Primer sequences used to amplify target sequences having various amplicon sizes

| Primer name | Amplicon size (bp) | SEQ ID NO | Sequence |
| --- | --- | --- | --- |
| Forward primer | — | SEQ ID NO: 3 | 5'-GTG TCT CTT ATC AGA CCG TT-3' |
| Reverse primer1 | 102 | SEQ ID NO: 4 | 5'-TGT AAT TCA GCT CCG CCA T-3' |
| Reverse primer2 | 198 | SEQ ID NO: 5 | 5'-CAA TTT GCG ACG GCG CG-3' |
| Reverse primer3 | 401 | SEQ ID NO: 6 | 5'-AAA TAA CGC CGG AAC ATT AGT-3' |
| Reverse primer4 | 805 | SEQ ID NO: 7 | 5'-TAA CAT GAG CTG TCT TCG GT-3' |
| Reverse primer5 | 1600 | SEQ ID NO: 8 | 5'-ACA TAA TGG TGC AGG GCG-3' |

Figure 8D:
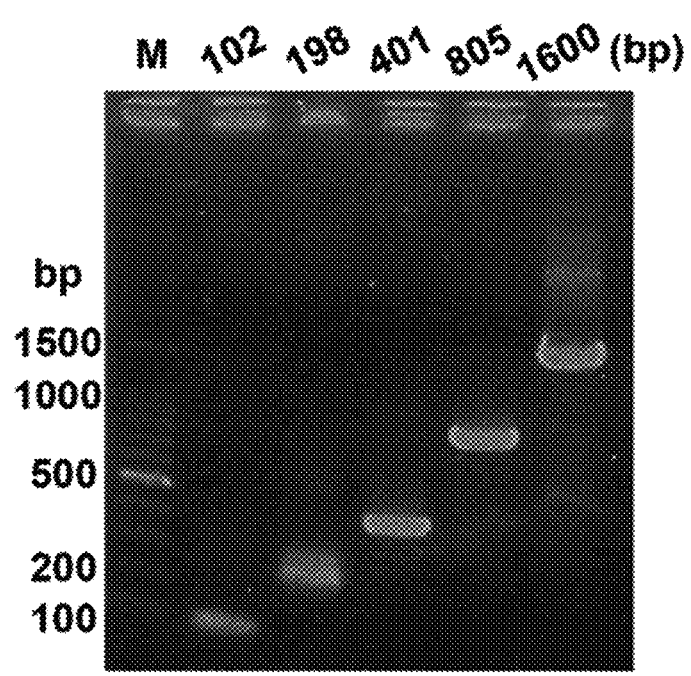

As a result, as shown in FIGS. 8B to 8D, in the case of samples containing no PEG-nGO were used, amplicon products obtained in the first round of PCR exhibited a distinct single band without nonspecific amplification, whereas, in amplicon products obtained in the second round of PCR, nonspecific amplification was generated and band smearing was observed when performing electrophoresis (FIG. 8C). On the other hand, in the case of samples containing 5 μg/ml of the PEG-nGO, PCR amplicons having various sizes were effectively amplified and no nonspecific DNA amplification was observed. In addition, when performing electrophoresis, smearing was not observed in bands corresponding to the amplicons (FIG. 8D). These results indicate that the specificity and efficiency of PCR may be significantly increased regardless of target amplicon size when the PEG-nGO is added under optimal conditions.

Therefore, the present invention provides a composition for PCR including PEG-nGO. The PEG-nGO included in the composition for PCR of the present invention functions as intracellular single-stranded binding proteins (SSBs) to bind to single-stranded DNA resulting from the denaturation of double-stranded DNA and to protect the same. The PEG-nGO can bind to single-stranded DNA and protect the same. Thus, the PEG-nGO is adsorbed to primers abundant in the early stage of PCR, and can reduce formation of primer dimers and nonspecific annealing between the primers and DNA templates. In addition, in the late stage of PCR, in which amplified PCR products are accumulated, the PEG-nGO effectively binds to single-stranded DNA resulting from denaturation of double-stranded DNA and can inhibit reannealing of amplified ssDNA, thereby promoting annealing between primers and DNA templates.

Therefore, the PEG-nGO of the present invention i) can increase the efficiency and specificity of PCR even in PCR proceeding in multiple rounds; ii) can improve PCR efficiency by inhibiting formation of primer dimers in a sample and improper annealing of primers at low annealing temperatures; iii) can reduce the time required for the denaturation step during PCR by promoting separation of double-stranded DNA templates, thereby effectively providing DNA templates and reducing the overall PCR run time; and iv) can also improve PCR efficiency in PCR for amplifying genes having various sizes. Thus, when using the PEG-nGO, the disadvantages that can occur in conventional PCR techniques can be overcome, and the efficiency and specificity of PCR can be improved.

What is claimed is:

1. A composition for polymerase chain reaction (PCR), comprising 6-arm polyethylene glycol-engrafted nano-sized graphene oxide (PEG-nGO), wherein the PEG-nGO has a thickness of 4 to 5 nanometers (nm).

2. The composition for PCR according to claim 1, wherein the PEG-nGO is present at a concentration of 1 to 10 μg/ml.

3. The composition for PCR according to claim 1, wherein each of a forward primer and a reverse primer is added to the composition for PCR at a concentration of 0.1 to 1.0 μM.

4. The composition for PCR according to claim 1, wherein the PEG-nGO increases efficiency and specificity of PCR by inhibiting primer dimerization and nonspecific binding of amplified amplicons.

5. The composition for PCR according to claim 1, wherein the PEG-nGO promotes denaturation of double-stranded DNA in a sample to shorten PCR time.

6. A polymerase chain reaction (PCR) kit, comprising the composition according to claim 1.

7. A polymerase chain reaction (PCR) method, comprising:

preparing a PCR sample by mixing a DNA template, dNTPs, a DNA polymerase, and forward and reverse primers for amplifying a target sequence with the composition for PCR according to claim 1; and performing PCR using the prepared PCR sample.

8. The PCR method according to claim 7, wherein, in the performing, PCR is selected from the group consisting of quantitative PCR (qPCR), real-time PCR, reverse transcription PCR (RT-PCR), solid phase PCR, competitive PCR, overlap-extension PCR, multiplex PCR, nested PCR, inverse PCR, ligation-mediated PCR, intersequence-specific PCR (ISSR), methylation-specific PCR (MSP), colony PCR, miniprimer PCR, nanoparticle-assisted PCR (nanoPCR), thermal asymmetric interlaced PCR (TAIL-PCR), touch-down PCR (step-down PCR), hot start PCR, in-silico PCR, allele-specific PCR, assembly PCR, asymmetric PCR, dial-out PCR, digital PCR (dPCR), and helicase-dependent amplification.

* * * * *